United States Patent
Lewis et al.

(10) Patent No.: US 12,233,081 B2
(45) Date of Patent: Feb. 25, 2025

(54) HYGROMYCIN A COMPOUNDS AND METHODS OF TREATING SPIROCHETE DISEASES

(71) Applicants: Kim Lewis, Newton, MA (US); Yu Imai, Boston, MA (US); Xiaoqian (Wendy) Wu, Boston, MA (US); Anthony D'Onofrio, Northborough, MA (US); Nadja Leimer, Schattdorf (CH); Akira Iinishi, Newton, MA (US)

(72) Inventors: Kim Lewis, Newton, MA (US); Yu Imai, Boston, MA (US); Xiaoqian (Wendy) Wu, Boston, MA (US); Anthony D'Onofrio, Northborough, MA (US); Nadja Leimer, Schattdorf (CH); Akira Iinishi, Newton, MA (US)

(73) Assignee: NORTHEASTERN UNIVERSITY, Boston, MA (US)

( * ) Notice: Subject to any disclaimer, the term of this patent is extended or adjusted under 35 U.S.C. 154(b) by 779 days.

(21) Appl. No.: 17/269,189

(22) PCT Filed: Aug. 19, 2019

(86) PCT No.: PCT/US2019/047031
§ 371 (c)(1),
(2) Date: Feb. 17, 2021

(87) PCT Pub. No.: WO2020/041179
PCT Pub. Date: Feb. 27, 2020

(65) Prior Publication Data
US 2021/0275559 A1    Sep. 9, 2021

Related U.S. Application Data

(60) Provisional application No. 62/719,983, filed on Aug. 20, 2018.

(51) Int. Cl.
*A61K 31/7048* (2006.01)
*A61P 31/04* (2006.01)

(52) U.S. Cl.
CPC .......... *A61K 31/7048* (2013.01); *A61P 31/04* (2018.01)

(58) Field of Classification Search
CPC ............................ A61K 31/7048; A61P 31/04
See application file for complete search history.

(56) References Cited

U.S. PATENT DOCUMENTS

| | | |
|---|---|---|
| 4,794,105 A | 12/1988 | Hasegawa et al. |
| 6,313,100 B1 | 11/2001 | Brighty et al. |
| 6,342,497 B1 | 1/2002 | Linde |
| 6,492,342 B1 | 12/2002 | Kaneko |
| 6,562,792 B1 | 5/2003 | Brighty et al. |
| 6,867,230 B2 | 3/2005 | Hayward et al. |

FOREIGN PATENT DOCUMENTS

| | | |
|---|---|---|
| EP | 0213692 A2 | 3/1987 |
| EP | 0236011 A2 | 9/1987 |
| WO | 1999057125 A2 | 11/1999 |

OTHER PUBLICATIONS

Guerrero et al., Eur. J. Biochem., 1980, 107, p. 409-414. (Year: 1980).*
Moody et al., Antimicrobial Agents and Chemotherapy, 1994, 38(7), p. 1567-1572. (Year: 1994).*
Baron. S., ed., Medical Microbiology, 1996, 4th ed., The University of Texas Medical Branch at Galveston, chapter 36 Treponema, 13 pages, accessed online at https://www.ncbi.nlm.nih.gov/ on Jun. 27, 2024. (Year: 1996).*
Butler et al., The Journal of Infectious Diseases, 1979, 140(5), p. 665-675. (Year: 1979).*
Extended European Search Report in EP Application No. 19852163. 5, mailed Jul. 20, 2022, 10 pages.
Pittenger, R. C. et al., "Hygromycin I. Preliminary Studies on the Production and Biologic Activity of a New Antibiotic," Antibiotic and Chemotherapy, 1953, 3:1268-1278.
International Search Report and Written Opinion for International Application No. PCT/US2019/047031 dated Nov. 15, 2019, 7 pages.
Jaynes et al. 'Synthesis and vitro antibacterial activity of hygromycin a analogs modified at the C4' aryl position' Bioorganic & Medicinal Chemistry Letters 1993 vol. 3 Issue 8 pp. 1531-1536.
Wakisaka et al. 'Hygromycin and Epihygromycin From a Bacterium Corynebacterium EQUI No. 2841' The Journal of Antibiotics 1980 vol. XXXIII No. 7 pp. 695-704.

* cited by examiner

*Primary Examiner* — Jonathan S Lau

(57) ABSTRACT

This invention provides, among other things, compounds useful for treating spirochete diseases such as Lyme disease, as well as pharmaceutical formulations and/or environmental baits containing such compounds.

20 Claims, No Drawings

HYGROMYCIN A COMPOUNDS AND METHODS OF TREATING SPIROCHETE DISEASES

CROSS-REFERENCE TO RELATED APPLICATION

This application is a U.S. National Phase Application of PCT/US2019/047031, filed Aug. 19, 2019, which claims priority to and the benefits of U.S. Provisional Patent Application No. 62/719,983, which was filed on Aug. 20, 2018. The entire disclosures of these priority documents are hereby incorporated by reference in their entireties.

BACKGROUND OF THE INVENTION

There is a need in the art for new compounds for, and new treatments and/or preventative measures against, diseases associated with spirochetes, such as Lyme disease.

The current standard of treatment for Lyme disease involves amoxicillin or ceftriaxone. These two antibiotics are known to significantly disrupt the gut microbiome of the individual being treated. Therapies which treat Lyme disease, without significantly disrupting the gut microbiome, would be an important advance.

Surprisingly, the inventors have discovered such a therapy. This embodiment, as well as others, are described herein.

SUMMARY OF THE INVENTION

The inventors have unexpectedly discovered that hygromycin A treats spirochete infections, such as Lyme disease, without significantly disrupting the gut microbiome.

In one aspect, the invention provides a method of treating a disease associated with a spirochete in an animal, comprising: administering to an animal in need of treatment thereof a therapeutically effective amount of a compound described herein, or a salt or a hydrate or a solvate thereof, thereby treating the disease associated with a spirochete.

In one aspect, the invention provides a method of treating a disease with a spirochete in an animal, comprising: administering to an animal in need of treatment thereof a therapeutically effective amount of a compound, or a salt or a hydrate or a solvate thereof, having a structure according to formula (I):

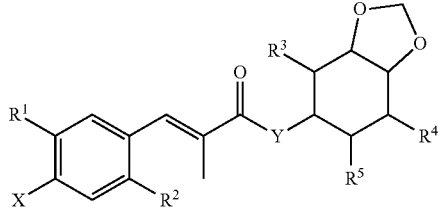

wherein $R^1$ is H or OH or halogen; $R^2$ is H or OH or halogen; $R^3$ is H or OH or halogen; $R^4$ is H or OH or halogen; $R^5$ is H or OH or halogen; Y is —O— or —NH— or —CH$_2$—; X is selected from the group consisting of

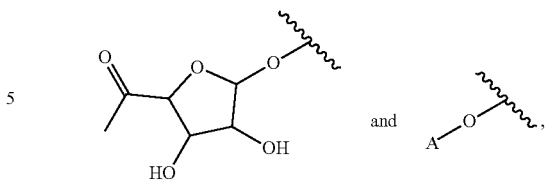

wherein A is $C_1$ or $C_2$ or $C_3$ or $C_4$ or $C_5$ or $C_6$ haloalkyl or $C_1$ or $C_2$ or $C_3$ or $C_4$ or $C_5$ or $C_6$ alkoxy or $C_1$ or $C_2$ or $C_3$ or $C_4$ or $C_5$ or $C_6$ alkyl, thereby treating the disease associated with a spirochete. In an exemplary embodiment, the spirochete is of the *Treponema* species, the *Leptospira* species, the *Borrelia* species, or the *Brachyspira* species. In an exemplary embodiment, the spirochete is of the *Borrelia* species. In an exemplary embodiment, the spirochete is *Borrelia burgdorferi*. In an exemplary embodiment, the disease associated wilt a spirochete is selected from the group consisting of leptospirosis, Lyme disease, relapsing fever, syphilis, yaws, intestinal spirochetosis, gingivitis and periodontitis. In an exemplary embodiment, the disease associated with a spirochete is Lyme disease. In an exemplary embodiment, the animal is a human. In an exemplary embodiment, the compound, or a salt or a hydrate or a solvate thereof, is

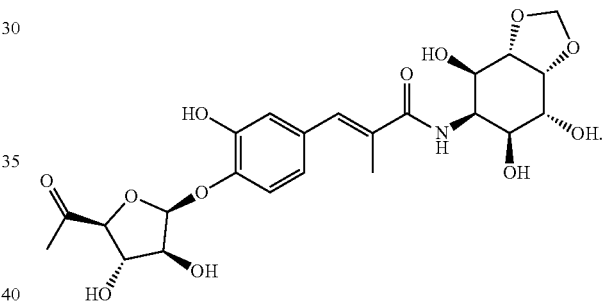

In an exemplary embodiment, the compound, or a salt or a hydrate or a solvate thereof, is

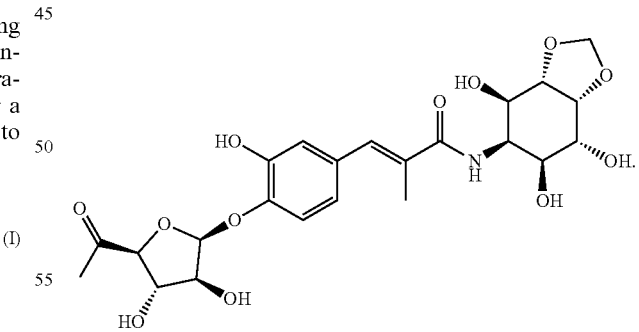

the disease associated with a spirochete is Lyme disease, and the animal is a human.

In an aspect, the invention provides a method of killing and/or preventing the growth of a spirochete, comprising: contacting ire spirochete with an effective amount of a compound described herein, thereby killing and/or preventing the growth of the spirochete.

In an aspect, the invention provides a method of killing and/or preventing the growth of a spirochete, comprising:

contacting the spirochete with an effective amount of a compound, or a salt or a hydrate or a solvate thereof, having a structure according to formula (I):

(I)

wherein R¹ is H or OH or halogen; R² is H or OH or halogen; R³ is H or OH or halogen; R⁴ is H or OH or halogen; R⁵ is H or OH or halogen; Y is —O— or —NH— or —CH₂—; X is selected from the group consisting of and wherein A is $C_1$ or $C_2$ or $C_3$ or $C_4$ or $C_5$ or $C_6$ haloalkyl or $C_1$ or $C_2$ or $C_3$ or $C_4$ or $C_5$ or $C_6$ alkoxy or $C_1$ or $C_2$ or $C_3$ or $C_4$ or $C_5$ or $C_6$ alkyl, thereby killing and/or preventing the growth of the spirochete. In an exemplary embodiment, the spirochete is of the *Treponema* species, the *Leptospira* species, the *Borrelia* species, or the *Brachyspira*, species. In an exemplary embodiment, the spirochete is selected from the group consisting of *Borrelia burgdorferi*, *Borrelia mayomii*, *Borrelia afzelii*, and *Borrelia garinii*. In an exemplary embodiment, the compound, or a salt or a hydrate or a solvate thereof, is In an exemplary embodiment, the spirochete is *Borrelia burgdorferi*, and the compound, or a salt or a hydrate or a solvate thereof, is In another aspect, the invention provides a compound, or a salt or a hydrate or a solvate thereof, having, a structure according to formula (I):

(I)

wherein R¹ is H or OH or halogen; R² is H or OH or halogen; R³ is H or OH or halogen; R⁴ is H or OH or halogen; R⁵ is H or OH or halogen; Y is —O— or —NH— or —CH₂—; X is selected from the group consisting of and wherein A is $C_1$ or $C_2$ or $C_3$ or $C_4$ or $C_5$ or $C_6$ haloalkyl or $C_1$ or $C_2$ or $C_3$ or $C_4$ or $C_5$ or $C_6$ alkoxy or $C_1$ or $C_2$ or $C_3$ or $C_4$ or $C_5$ or $C_6$ alkyl and wherein the compound is not

DETAILED DESCRIPTION OF THE INVENTION

I. Definitions and Abbreviations

As used herein, the singular forms "a", "an", and "the" include plural references unless the context clearly dictates otherwise. For example, reference to "an active agent" includes a single active agent as well as two or more different active agents in combination. It is to be understood that present teaching is not limned to the specific dosage forms, carriers, or the like, disclosed herein and as such may vary.

The abbreviations used herein generally have their conventional meaning within the chemical and biological arts.

The following abbreviations have been used: Ac is acetyl; AcOH is acetic acid; ACTBr is cetyltrimethylammonium bromide; AIBN is azobisisobutyronitrile or 2,2 azobisisobutyronitrile; aq. is aqueous; Ar is aryl; $B_2pin_2$ is bis(pinacolato)diboron; Bn is, in general, benzyl [see Cbz for one example of an exception], $(BnS)_2$ is benzyl disulfide, BnSH is benzyl thiol or benzyl mercaptan; BnBr is benzyl bromide; Boc is tert-butoxy carbonyl; $Boc_2O$ is di-tert-butyl dicarbonate; Bz is, in general, benzoyl; BzOOH is benzoyl peroxide; Cbz or Z is benzyloxycarbonyl or carboxybenzyl; $Cs_2CO_3$ is cesium carbonate; CSA is camphor sulfonic acid; CTAB is cetyltrimethylammonium bromide; Cy is cyclohexyl; DABCO is 1,4-diazabicyclo[2.2.2]octane; DCM is dichloromethane or methylene chloride; DHP is dihydropyran; DIAD is diisopropyl azodicarboxylate; DIEA or DIPEA is N,N-diisopropylethylamine; DMAP is 4-(dimethylamino) pyridine; DME is 1,2-dimethoxyethane; DMF is N,N-dimethylformamide; DMSO is dimethylsulfoxide; equiv or eq. is equivalent; EtOAc is ethyl acetate; EtOH is ethanol; $Et_2O$ is diethyl ether; EDCI is N-(3-dimethylaminopropyl)-N'-ethylcarbodiimide hydrochloride; ELS is evaporative light scattering; equiv or eq is equivalent; h is hours; HATU is O-(7-azabenzotriazol-1-yl-N,N,N',N'-tetramethyluronium hexafluorophosphate; HOBt is N-hydroxybenzotriazole; HCl is hydrochloric acid; HPLC is high pressure liquid chromatography; ISCO Companion is automated flash chromatography equipment with fraction analysis by UV absorption available from Presearch; KOAc or AcOK is potassium acetate; $K_2CO_3$ is potassium carbonate; $LiAlH_4$ or LAH is lithium aluminum hydride; LDA is lithium diisopropylamide; LHMDS is lithium bis(trimethylsilyl) amide; KHMDS is potassium bis(trimethylsilyl) amide; LiOH is lithium hydroxide; m-CPBA is 3-chloroperoxybenzoic add; MeCN or ACN is methyl cyanide or cyanomethane or ethanenitrile or acetonitrile which are all names for the same compound; MeOH is methanol; $MgSO_4$ is magnesium sulfate; mins or min is minutes; Mp or MP is melting point; $NaCNBH_3$ is sodium cyanoborohydride; NaOH is sodium, hydroxide; $Na_2SO_4$ is sodium sulfate; NBS is N-bromosuccinimide; $NH_4Cl$ is ammonium chloride; NIS is N-iodosuccinimide; $N_2$ is nitrogen; NMM is N-methylmorpholine; n-BuLi is n-butyllithium; overnight is O/N; $PdCl_2$(pddf) is 1,1'-Bis (diphenylphosphino) ferrocene]dichloropalladium(II); Pd/C is the catalyst known as palladium on carbon, $Pd_2(dba)_3$ is an organometallic catalyst known as tris(dibenzylideneacetone) dipalladium(0); RaNi or Raney Ni is Raney nickel; Ph is phenyl; PMB is p-methoxy benzyl; PrOH is 1-propanol; iPrOH is 2-propanol; $POCl_3$ is phosphorus chloride oxide; PTSA is para-toluene sulfonic acid; Pyr. or Pyr or Py as used herein means pyridine; RT or rt or r.t. is room temperature; sat. is saturated; Si-amine or Si—$NH_2$ is amino-functionalized silica, available from SiliCycle; Si-pyr is pyridyl-functionalized silica, available from SiliCycle; TEA or $Et_3N$ is triethylamine; TEA is trifluoroacetic acid; $Tf_2O$ is trifluoromethanesulfonic anhydride; THF is tetrahydrofuran; TFAA is trifluoroacetic anhydride; THP is tetrahydropyranyl; TMSI is trimethylsilyl iodide; $H_2O$ is water; $diNO_2PhSO_2Cl$ is dinitrophenyl sulfonyl chloride, 3-F-4-$NO_2$-$PhSO_2Cl$ is 3-fluoro-4-nitrophenylsulfonyl chloride; 2-MeO-4-$NO_2$-$PhSO_2Cl$ is 2-methoxy-4-nitrophenylsulfonyl chloride; and $(EtO)_2POCH_2COOEt$ is a triethylester of phosphonoacetic acid known as diethyl phosphonoacetate.

"Compound of the invention," as used herein refers to the compounds discussed herein, salts (e.g. pharmaceutically acceptable salts), solvates and hydrates of these compounds.

Where substituent groups are specified by their conventional chemical formulae, written From left to right they equally encompass the chemically identical substituents, which would result from writing the structure from right to left, e.g., —$CH_2O$— is intended to also recite —$OCH_2$—.

The term "poly" as used herein means at least 2. For example, a polyvalent metal ion is a metal ion having a valency of at least 2.

"Moiety" refers to a radical of a molecule that is attached to the remainder of the molecule.

The symbol ⁓, whether utilized as a bond or displayed perpendicular to a bond, indicates the point at which the displayed moiety is attached to the remainder of the molecule.

The term "alkyl," by itself or as part of another substituent, means, unless otherwise stated, a straight or branched chain, or cyclic hydrocarbon radical, or combination thereof, which may be frilly saturated, mono- or polyunsaturated and can include di- and multivalent radicals, having the number of carbon atoms designated (i.e. $C_1$-$C_{10}$ means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclobutyl, cyclohexyl, (cyclohexyl)methyl, cyclopropyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the invention. A "lower alkyl" or "lower alkylene" is a shorter chain alkyl or alkylene group, generally having eight or fewer carbon atoms.

The term "alkenylene" by itself or as part of another substituent means a divalent radical derived from an alkene.

The term "cycloalkylene" by itself or as part of another substituent means a divalent radical derived from a cycloalkane.

The term "heteroalkylene" by itself or as part of another substituent means a divalent radical derived from an heteroalkane.

The term "heterocycloalkylene" by itself or as part of another substituent means a divalent radical derived from an heterocycloalkane.

The term "arylene" by itself or as part of another substituent means a divalent radical derived from an aryl.

The term "heteroarylene" by itself or as part of another substituent means a divalent radical derived from heteroaryl.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized, and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —O—CH$_3$, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like) Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl" by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cydohexyl, 1-cyclohexenyl, 3-cyclohexenyl, cycloheptyl, and the like. Examples of heterocycloalkyl include, but are not limited to, 2-(4-methylpiperazin-1-yl)ethyl, 3-(4-methylpiperazin-1-yl)propyl, 2-morpholinoethyl, 3-morpholinopropyl, 1-methylazetidin-3-yl, 1-ethylazetidin-3-yl, 1-isopropylazetidin-3-yl, 1-methylpiperidin-4-yl, 1-ethylpiperidin-4-yl or, 1-isopropylpiperidin-4-yl, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 2-fluoroethyl, 2,2-difluoroethyl, 2-chloroethyl, 3-chloropropyl, 4-chlorobutyl, 3-bromopropyl, and the like.

The term "aryl" means, unless otherwise stated, a poly unsaturated, aromatic, substituent that can be a single ring or multiple rings (preferably from 1 or 2 or 3 rings), which are fused together or linked covalently. The term "heteroaryl" refers to aryl groups (or rings) that contain from one to four heteroatoms. In an exemplary embodiment, the heteroatom is selected from B, N, O, and S, wherein, the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazoiyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are genetically referred to as "alkyl group substituents," and they can be one or more of a variety of groups selected from, but not limited to: —R', —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR'''', —C(NR'R'R''')=NR''', —NR''''—C(NR'R") =NR''', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to (2m'+1), where m' is the total number of carbon atom in such radical. R', R", R''', R'''' and R''''' each preferably independently refer to hydrogen, substituted or unsubstituted haloalkyl, substituted or unsubstituted heteroalkyl, substituted or unsubstituted heterocycloalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"', R"" and R""' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: —R', —OR', =O, =NR', =N—OR', —NR'R", —SR', -halogen, —SiR"R"R"', —OC(O)R', —C(O)R', —CO$_2$R', —CONR'R", —OC(O)NR'R", —NR"C(O)R', —NR'—C(O)NR'R"', —NR"C(O)$_2$R', —NR""—C(NR'R"R"')=NR"", —NR""—C(NR'R") =NR"', —S(O)R', —S(O)$_2$R', —S(O)$_2$NR'R", —NR"SO$_2$R', —CN, —NO$_2$, —N$_3$, —CH(Ph)$_2$, fluoro(C$_1$-C$_4$)alkoxy, and fluoro(C$_1$-C$_4$)alkyl, in a number ranging from zero to the total number of open valences on the aromatic, ring system; and where R', R", R"', R"" and R""' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"', R"" and R""' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R"')$_d$—, where s and d are independently integers of from 0 to 3, and X is —O—, —NR'—, —S—, —S(O)—, —S(O)$_2$—, or —S(O)$_2$NR'—. The substituents R', R", R"' and R"" are preferably independently selected from hydrogen or substituted or unsubstituted C$_1$ or C$_2$, or C$_3$ or C$_4$ of C$_5$ or C$_6$ alkyl.

"Ring" as used herein, means a substituted or unsubstituted cycloalkyl, substituted or unsubstituted heterocycloalkyl, substituted or unsubstituted aryl, or substituted or unsubstituted heteroaryl, A ring includes fused, ring moieties. The number of atoms in a ring is typically defined by the number of members in the ring. For example, a "5- to 7-membered ring" means there are 5 or 6 or 7 atoms in the encircling arrangement. Unless otherwise specified, the ring optionally includes a heteroatom. Thus, the term "5 to 7-membered ring" or "5 or 6 or 7 membered ring" includes, for example phenyl, pyridinyl and piperidinyl. The term "5 to 7-membered heterocycloalkyl ring" "5 or 6 or 7-membered heterocycloalkyl ring", on the other hand, would include pyridinyl and piperidinyl, but not phenyl. The term "ring" further includes a ring system composing more than one "ring", wherein each "ring" is independently defined as above.

As used herein, the term "heteroatom" includes atoms other than carbon (C) and hydrogen (H). Examples include oxygen (O), nitrogen (N) sulfur (S), silicon (Si), germanium (Ge), and aluminum (Al).

The term "leaving group" means a functional group or atom which can be displaced by another functional group, or atom in a substitution reaction, such as a nucleophilic substitution reaction. By way of example, representative leaving groups include Inflate, chloro, bromo and iodo groups, sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local of systemic effect. A "Topically effective," "pharmaceutically effective," or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino (such as choline or diethylamine or amino acids such as d-arginine, l-arginine, d-lysine, or l-lysine), or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or add and isolating the parent compounds in the conventional manner. The parent form of the compound differs from the various salt forms in certain physical properties, such as solubility in polar solvents.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the invention. The graphic representations of racemic, ambiscalemic and scalemic or enantiomeric ally pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known, in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) winch is incorporated herein by reference.

The term "pharmaceutically acceptable additive" refers to preservatives, antioxidants, fragrances, emulsifiers, dyes and excipients known or used in the field of drug formulation and that do not unduly interfere with the effectiveness of the biological activity of the active agent, and that is sufficiently non-toxic to the host or patient. Additives for topical formulations are well-known in the art, and may be added to the topical composition, as long as they are pharmaceutically acceptable and not deleterious to the epithelial cells or their function. Further, they should not cause deterioration in the stability of the composition. For example, inert fillers, anti-irritants, tackifiers, excipients, fragrances, opacifiers, antioxidants, gelling agents, stabilizers, surfactant, emollients, coloring agents, preservatives, buffering agents, other permeation enhancers, and other conventional components of topical or transdermal delivery formulations as are known in the art.

The term "excipients" is conventionally known to mean carriers, diluents and/or vehicles used m formulating drug compositions effective tor the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" means moieties or compounds that are, within the scope of medical judgment, suitable for use in humans without causing undesirable biological effects such as undue toxicity, irritation, allergic response, and the like, for example.

The phrase "oral dosage form" means any pharmaceutical formulation administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. Amoral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package. In a preferred embodiment, the oral dosage form is one, two or three units. In a particularly preferred embodiment, the oral dosage form is one unit.

The phrase "unit", as used herein, refers to the number of discrete objects to be administered which comprise the dosage form. In some embodiments, the dosage form includes a compound of the invention in one capsule. This is a single unit. In some embodiments, the dosage form includes a compound of the invention as part of a therapeutically effective dosage of a cream or ointment. This is also a single unit. In some embodiments, the dosage form includes a compound of the invention and another active ingredient contained within one capsule, or as part of a therapeutically effective dosage of a cream or ointment. This is a single unit, whether or not the interior of the capsule includes multiple discrete granules of the active ingredient. In some embodiments, the dosage form includes a compound of the invention in one capsule, and the active ingredient in a second capsule. This is a two unit dosage form, such as two capsules or tablets, and so such units are contained in a single package. Thus the term 'unit' refers to the object which is administered to the animal, not to the interior components of the object.

"Biological medium," as used herein refers to both in vitro and in vivo biological milieus. Exemplary in vitro "biological media" include, but are not limited to, cell culture, tissue culture, homogenates, plasma and blood. In vivo applications are generally performed in mammals, preferably humans.

"Inhibiting" is used herein to refer to the partial or full blockade of the growth of a spirochete described herein.

Embodiments of the invention also encompass compounds that are poly- or multi-valent species, including, for example, species such as dimers, trimers, tetramers and higher homologs of the compounds of use in the invention or reactive analogues thereof.

II. Introduction

The invention provides new compounds, as well as new treatments and/or preventative measures against diseases associated with spirochetes, such as Lyme disease. The invention also provides compounds winch can be incorporated in environmental baits.

III. The Compounds

In one aspect, the invention provides a compound of the invention. In an exemplary embodiment, the invention is a compound described herein. In an exemplary embodiment, the invention is a compound according to a formula described herein.

In another aspect, the invention provides a compound, or a salt or a hydrate or a solvate thereof, having a structure according to formula (I):

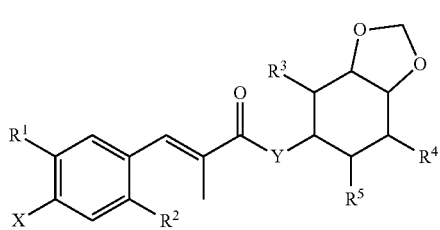

(I)

wherein $R^1$ is H or OH or halogen; $R^2$ is H or OH or halogen; $R^3$ is H or OH or halogen; $R^4$ is H or OH or halogen; $R^5$ is H or OH or halogen; Y is —O— or —NH— or —CH$_2$—, X is selected from the group consisting of

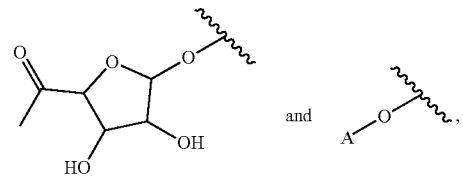

and wherein A is $C_1$ or $C_2$ or $C_3$ or $C_4$ or $C_5$ or $C_6$ haloalkyl or $C_1$ or $C_2$ or $C_3$ or $C_4$ or $C_5$ or $C_6$ alkoxy or $C_1$ or $C_2$ or $C_3$ or $C_4$ or $C_5$ or $C_6$ alkyl.

In another aspect the invention provides a compound, or a salt or a hydrate or a solvate thereof, wherein X, Y, $R^1$, $R^2$, $R^3$, $R^4$, and $R^5$ are as described herein, and having a structure which is a member selected from the group consisting of:

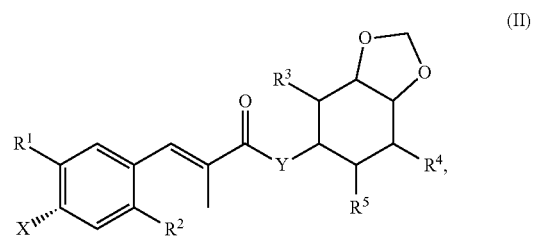

(II)

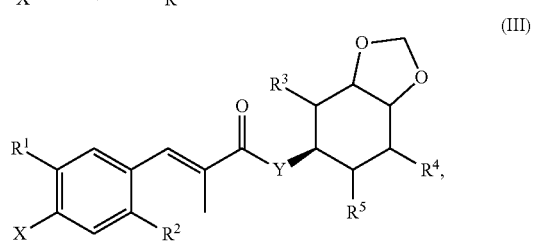

(III)

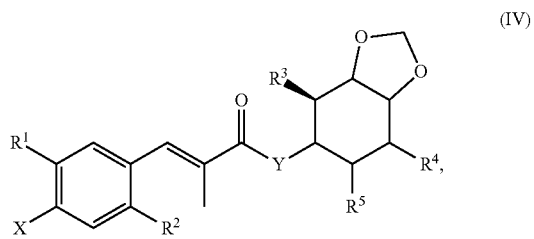

(IV)

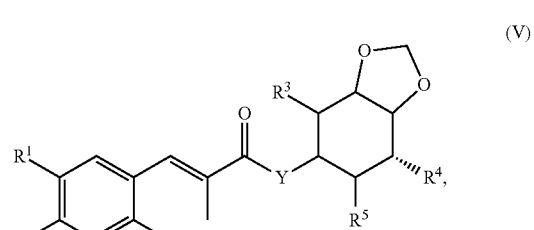

(V)

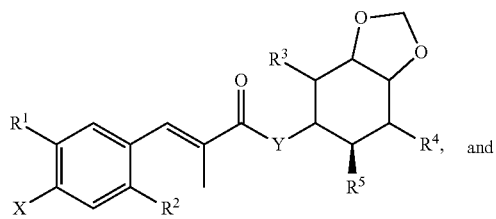

(VI)

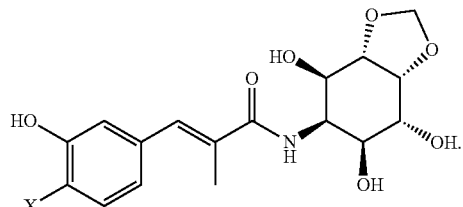

(X)

In another aspect, the invention provides a compound, or a sail or a hydrate or a solvate thereof, wherein X, Y, $R^3$, $R^4$, and $R^5$ are as described herein, and having a structure which is

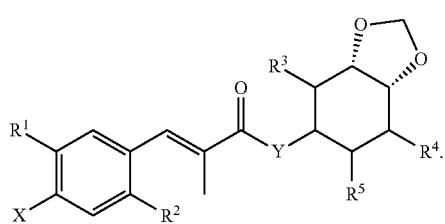

(VII)

In another aspect, the invention provides a compound, or a salt or a hydrate or a solvate thereof, wherein X, Y, $R^1$, $R^2$, $R^3$, $R^4$, and $R^5$ are as described herein, and having a structure which is

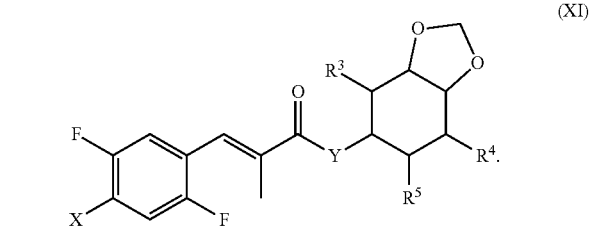

(XI)

In another aspect, the compound or a salt or a hydrate or a solvate thereof, has a structure according for a formula described herein, wherein $R^1$, $R^2$, $R^3$, $R^4$, $R^5$, and Y are as described herein, and X is a member selected from

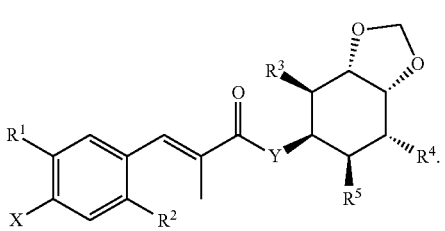

(VIII)

In another aspect, the invention provides a compound, or a salt or a hydrate or a solvate thereof, wherein X is as described herein, and having a structure which is

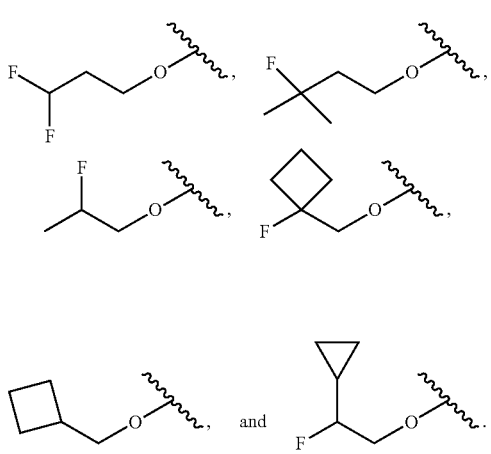

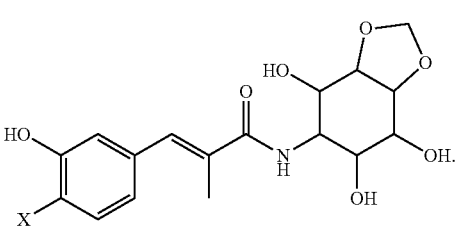

(IX)

In another aspect, the invention provides a compound, or a salt or a hydrate or a solvate thereof, wherein X is as described herein, and having a structure which is In another aspect, the invention provides a compound, or a salt or a hydrate or a solvate thereof, wherein X, Y, $R^3$, $R^4$, and $R^5$ are as described herein, and having a structure winch is

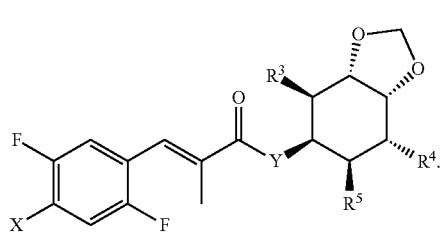
(XII)

In another aspect, the invention provides a compound, or a salt or a hydrate or a solvate thereof, wherein X, Y, $R^3$, $R^4$, and $R^5$ are as described herein, and having a structure which is

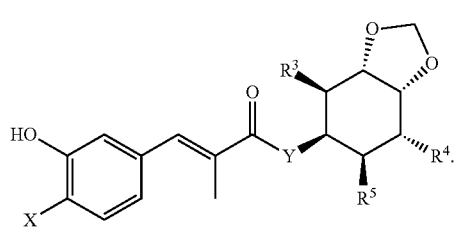
(XIII)

In another aspect, the invention provides a compound, or a salt or a hydrate or a solvate thereof, wherein X is as described herein, and having a structure which is

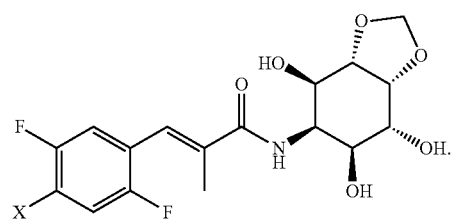
(XIV)

In another aspect the invention provides a compound, or a salt or a hydrate or a solvate thereof, wherein X is as described herein, and having a structure which is

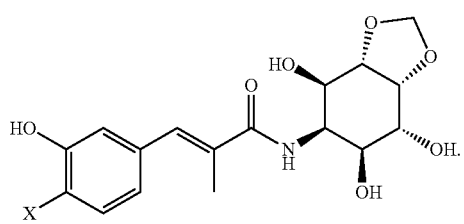
(XV)

In another aspect, the invention provides a compound, or a salt or a hydrate or a solvate thereof, having a structure which is

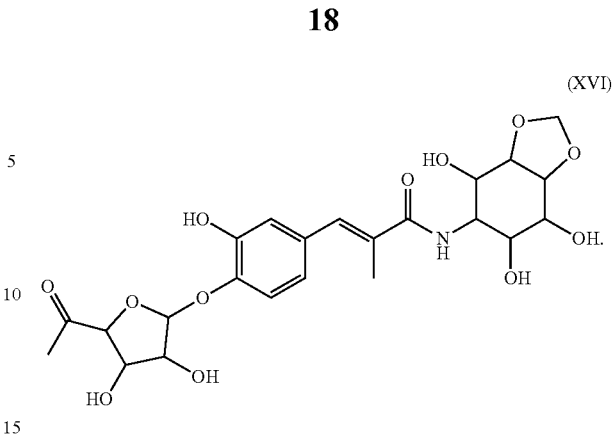
(XVI)

In another aspect, the invention provides a compound, or a salt or a hydrate or a solvate thereof, having a structure which is

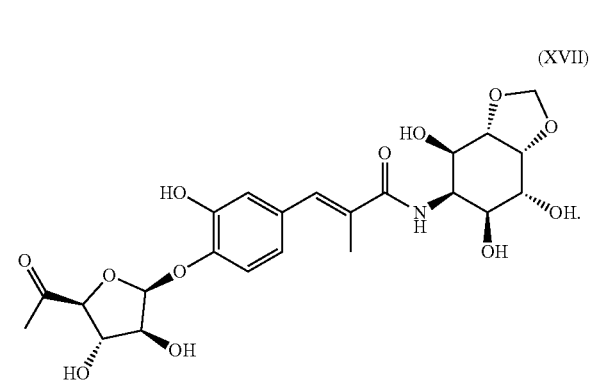 [SMILES: CC(=O)[C@H]1O[C@@H](Oc2ccc(/C=C(\C)C(=O)N[C@@H]3[C@H](O)[C@@H](O)[C@H]4OCO[C@H]4[C@@H]3O)cc2O)[C@@H](O)[C@@H]1O]
(XVII)

In an exemplary embodiment, the invention provides a compound described herein, or a salt, hydrate or solvate thereof, or a combination thereof. In an exemplary embodiment, the invention provides a compound described herein, or a salt, hydrate or solvate thereof. In an exemplary embodiment, the invention provides a compound described herein, or a salt thereof. In an exemplary embodiment, the salt is a pharmaceutically acceptable salt. In an exemplary embodiment, the invention provides a compound described herein, or a hydrate thereof. In an exemplary embodiment, the invention provides a compound described herein, or a solvate thereof. In an exemplary embodiment, the invention provides a salt of a compound described herein. In an exemplary embodiment, the invention provides a pharmaceutically acceptable salt of a compound described herein. In an exemplary embodiment, the invention provides a hydrate of a compound described herein. In an exemplary embodiment, the invention provides a solvate of a compound described herein.

IV. Methods and Uses

IV. a) Inhibiting Spirochete Growth or Killing a Spirochete

The compounds of the invention exhibit potency against spirochetes, and therefore have the potential to treat, and/or prevent a spirochete infection, or kill and/or inhibit the growth of a spirochete.

In another aspect, the spirochete is inside, or on the surface of an animal. In another exemplary embodiment, the animal is described herein. In another exemplary embodiment, the animal is a human.

In an exemplary embodiment, the spirochete infection is treated and/or prevented, or the spirochete is killed or its growth is inhibited, through oral administration of the compound of the invention. In an exemplary embodiment, the spirochete infection is treated and/or prevented, or the spirochete is killed or its growth is inhibited through intravenous administration of the compound of the invention.

In an exemplary embodiment, the spirochete is selected from the group consisting of the Leptospirales, order, the Brachyspirales order, the Brevinematales order, and the Spirochaetales order. In an exemplary embodiment, the spirochete is selected from the group consisting of the Leptospiraceae family, the Brachyspiraceae family, the Brevinemataceae family, the Borreliaceae family, and the Spirochaetaceae family. In an exemplary embodiment, the spirochete is selected from the group consisting of the Leptospiraceae family, the Brachyspiraceae family, the Brevinemataceae family, the Borreliaceae family, and the Spirochaetaceae family. In an exemplary embodiment, the spirochete is selected from the group consisting of the *Leptonema* genus, the *Leptospira* genus, the *Turneriella* genus, the *Brachyspira* genus, the *Brevinema* genus, the *Exilispira* genus, the *Borreliella* genus, the *Borrelia* genus, the *Cristispira pectinis* genus, the *Clevelandina reticulitermitidis* genus, the *Diplocalyx calotermitidis* genus, the *Hollandina pterotermitidis* genus, the *Pillotina calotermitidis* genus, the *Spironema culicis* genus, tire *Spirochaeta* genus, and the *Treponema* genus. In an exemplary embodiment, the spirochete is of the *Treponema* genus. In an exemplary embodiment, the spirochete is of the *Leptospira* genus. In an exemplary embodiment, the spirochete is of the *Borrelia* genus. In an exemplary embodiment, the spirochete is of the *Brachyspira* genus.

In an exemplary embodiment, the spirochete is *Borrelia burgdorferi*. In an exemplary embodiment, the spirochete is *Borrelia mayonii*. In an exemplary embodiment, the spirochete is *Borrelia afzelii*. In an exemplary embodiment, the spirochete is *Borrelia garinii*. In an exemplary embodiment, the spirochete is *Borrelia recurrentis*. In an exemplary embodiment, the spirochete is *Treponema pallidum*. In an exemplary embodiment, the spirochete is *Brachyspira pilosicoli*. In an exemplary embodiment the spirochete is *Brachyspira aalborgi*.

IV. b) Spirochete Infection

The compounds of the invention exhibit potency against spirochete, and therefore have the potential to be used to treat and/or prevent a spirochete infection.

In a further aspect, the invention provides a method of treating and/or preventing a spirochete infection, or a method of killing and/or inhibiting the growth of a spirochete, said method comprising: contacting said spirochete with an effective amount of a compound of the invention, thereby killing and/or inhibiting the growth of the spirochete.

In a further aspect, the invention provides a method of treating a spirochete infection comprising administering to an animal suffering from the infection an effective amount of a compound of the invention, or a pharmaceutically acceptable salt thereof, thereby treating the spirochete infection.

In a further aspect, the invention provides a method of preventing a spirochete infection comprising administering to an animal a prophylactic amount of a compound of the invention, or a pharmaceutically acceptable salt thereof, thereby preventing the spirochete infection.

IV. c) Diseases

The compounds of the invention exhibit potency against spirochetes, and therefore have the potential to achieve therapeutic efficacy in the animals described herein.

In another aspect, the invention provides a method of treating and/or preventing a disease. In an exemplary embodiment, the method includes administering to the animal a therapeutically effective amount of a compound of the invention, thereby treating and/or preventing the disease. In an exemplary embodiment, the compound of the invention can be used in human or veterinary medical therapy, particularly in the treatment or prophylaxis of spirochete-associated disease. In an exemplary embodiment, the compound is described herein, or a salt, hydrate or solvate thereof, or a combination thereof. In an exemplary embodiment, the invention provides a compound described herein. In an exemplary embodiment, the invention provides a compound described herein, or a salt, hydrate or solvate thereof. In an exemplary embodiment, the invention provides a compound described herein, or a salt thereof. In another exemplary embodiment, the compound of the invention is a compound described herein, or a pharmaceutically acceptable salt thereof. In an exemplary embodiment, the compound is a compound described herein, or a pharmaceutically acceptable salt thereof. In an exemplary embodiment, the compound is according to a formula described herein, or a pharmaceutically acceptable salt thereof. In an exemplary embodiment, the compound is part of a combination described herein. In an exemplary embodiment, the compound is part of a pharmaceutical formulation described herein. In another exemplary embodiment, the disease is a systemic disease. In another exemplary embodiment, the disease is a topical disease. In an exemplary embodiment, the animal being administered the compound is not otherwise in need of treatment with the compound.

In an exemplary embodiment, the disease is treated through oral administration of a compound of the invention and/or a combination of the invention. In an exemplary embodiment, the disease is treated through intravenous administration of a compound of the invention and/or a combination of the invention. In an exemplary embodiment, the disease is treated through subcutaneous administration of a compound of the invention and/or a combination of the invention.

In another exemplary embodiment, the disease is associated with a spirochete described herein. In an exemplary embodiment, the disease is associated with a *Treponema* species. In an exemplary embodiment, the disease is associated with a *Leptospira* species. In an exemplary embodiment, the disease is associated with a *Borrelia* species. In an exemplary, embodiment, the disease is associated with a *Brachyspira* species. In another exemplary embodiment, the disease is leptospirosis. In another exemplary embodiment, the disease is Lyme disease. In another exemplary embodiment, the disease is relapsing fever. In another exemplary embodiment, the disease is syphilis. In another exemplary embodiment, the disease is yaws. In another exemplary embodiment, the disease is intestinal spirochetosis. In another exemplary embodiment, the disease is gingivitis of periodontitis.

In an exemplary embodiment, for any of the methods described herein, the animal is selected from the group consisting of human, cattle, deer, reindeer, goat, honey bee, pig, sheep, horse, cow, bull, dog, guinea pig, gerbil, rabbit, cat, camel, yak, elephant, ostrich, otter, chicken, duck, goose, guinea fowl, pigeon, swan, and turkey. In another exemplary embodiment, for any of the methods described herein, the animal is selected from the group consisting of a human, cattle, goat, pig, sheep, horse, cow, bull, dog, guinea pig, gerbil, rabbit, cat, chicken and turkey. In another exemplary embodiment, for any of the methods described herein, the animal is a human.

In an exemplary embodiment, for any of the methods described herein, a compound of the invention, a compound described herein or a pharmaceutically acceptable salt thereof, and/or a pharmaceutical formulation described herein can be used.

V. Pharmaceutical Formulation

In another aspect, the invention provides a pharmaceutical formulation comprising: a) a compound of the invention; and b) a pharmaceutically acceptable excipient. In an exemplary embodiment, the compound is according to a formula described herein. In an exemplary embodiment, the compound is according to an example described herein. In an exemplary embodiment, the compound of the invention is a compound described herein, or a pharmaceutically acceptable salt thereof. In an exemplary embodiment, the compound of the invention is a compound described herein.

In an exemplary embodiment, the compound of the invention is present in the pharmaceutical formulation in an amount of between about 0.0001% to about 60% (w/w). In an exemplary embodiment, the amount is between about 0.01% to about 10% (w/w). In an exemplary embodiment, the amount is between about 0.1% to about 10% (w/w). In an exemplary embodiment, the amount is between about 0.25% to about 6% (w/w). In an exemplary embodiment, the amount is between about 0.5% to about 5% (w/w). In an exemplary embodiment, the amount is between about 0.1% and about 1.0% (w/w). In an exemplary embodiment, the amount is between about 1.0% and about 2.0% (w/w). In an exemplary embodiment, the amount is between about 2.0% and about 3.0% (w/w). In an exemplary embodiment the amount is between about 3.0% and about 4.0% (w/w). In an exemplary embodiment the amount is between about 4.0% and about 5.0% (w/w).

The pharmaceutical formulations of the invention can take a variety of forms adapted to the chosen route of administration. Those skilled in the art will recognize various synthetic methodologies that may be employed to prepare non-toxic pharmaceutical formulations incorporating the compounds described herein. Those skilled in the art will recognize a wide variety of non-toxic pharmaceutically acceptable solvents that may be used to prepare solvates of the compounds of the invention, such as water, ethanol, propylene glycol, mineral oil, vegetable oil and dimethyl sulfoxide (DMSO).

The compositions of the invention may be administered orally, topically, parenterally, by inhalation or spray or rectally in dosage unit formulations containing conventional non-toxic pharmaceutically acceptable carders, adjuvants and vehicles. It is further understood that the best method of administration may be a combination of methods. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques.

The pharmaceutical formulations containing compounds of the invention are preferably in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical formulations, and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; lubricating agents, for example magnesium stearate, stearic acid or talc; and extenders and bulking agents, such as macrocrystalline cellulose. The tablets may be uncoated or they may be coated by known techniques to delay disintegration and absorption in the gastrointestinal tract and thereby provide, a sustained action over a longer period. For example, a time delay material, such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; and dispersing or wetting agents, which may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetenol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Other dispersing agents include hydrophilic polymers, electrolytes, Tween™ 60 or 80, PEG, polyvinylpyrrolidone (PVP; commercially known as Plasdone™), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone™, e.g., S-630), 4-(1,1,3,3-tetramethylbutyl)-phenol polymer with ethylene oxide and formaldehyde (also known as tyloxapol), poloxamers (e.g., Pluronics F68™, F88™, and F108™, which are block copolymers of ethylene oxide and propylene oxide); and poloxamines (e.g., Tetronic 9080, also known as Poloxamine 9080, which is a tetrafunctional block copolymer derived from sequential addition of propylene oxide and ethylene oxide to ethylenediamine (BASF Corporation, Parsippany, N.J.)). Additional excipients, for example sweetening, flavoring and coloring agents, may also be present.

Pharmaceutical formulations of the invention may also be in the form of oil-in-water emulsions and water-in-oil emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth; naturally-occurring phosphatides, for example soy bean, lecithin, and esters or partial esters derived from Fatty acids and hexitol; anhydrides, for example sorbitan monooleate; and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical formulations may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In a preferred embodiment, the methods' of the invention can be employed through the topical application of the compounds described herein. Topical administration includes for example, transmucosal, transdermal, ungual and transungual routes of administration. The topical compositions useful in the subject invention can be made into a wide variety of product types. These include, but are not limited to, lotions, creams, gels, sticks, sprays, ointments, pastes, foams, mousses, masks, eye ointments, eye or ear drops, impregnated dressings, wipes, cleansers including soaps, body washes and shampoos, and make-up products, such as bases, blushes, lipsticks, and ewe shadows, among others. These product types can comprise several types of carrier systems including, but not limited to particles, nanoparticles, and liposomes. If desired, disintegrating agents can be added, such as the cross-linked polyvinyl pyrrolidone, agar or alginic acid or a salt thereof such as sodium alginate. Techniques for formulation and administration can be found in *Remington: The Science and Practice of Pharmacy*, supra. The formulation can be selected to maximize delivery to a desired target site in the body. The formulations can also include various conventional colorants, fragrances, thickeners, preservatives, humectants, emollients, demulcents, solubilizing excipients, dispersants, penetration enhancers, plasticizing agents, preservatives, stabilizers, demulsifiers, wetting agents, sunscreens, emulsifiers, moisturizers, astringents, deodorants, and the like, which can be added to provide additional benefits such as, for example, improving the feel and/or appearance of the topical preparation.

The composition of the invention may also be administered in the form of suppositories, e.g., for rectal administration of the drug. These compositions can be prepared by mixing the drag with a suitable non-irritating excipient that is solid at ordinary temperatures but liquid at the rectal temperature and will therefore melt in the rectum to release the drug. Such materials are cocoa butter and polyethylene glycols.

Alternatively, the compositions can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition containing the therapeutic compound may be added to the animal's feed or drinking water. Also, it will be convenient to formulate animal feed and drinking wafer products so that the animal takes in an appropriate quantity of the compound in its diet. It will further be convenient to present the compound in a composition as a premix for addition to the feed or drinking water. The composition can also be added as a food or drink supplement for humans.

Dosage levels of the order of from about 5 mg to about 250 mg per kilogram of body weight per day and more preferably from about 25 mg to about 150 mg per kilogram of body weight per day, are useful in the treatment of the above-indicated conditions. The amount of active ingredient that may be combined with the carrier materials to produce a single dosage form will vary depending upon the condition being treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

Preferred compounds of the invention will have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

The amount of the composition required for use in treatment will vary not only with the particular compound selected but also with the route of administration, the nature of the condition being treated and the age and condition of the patient and will ultimately be at the discretion of the attendant physician or clinician.

In an exemplary embodiment, the pharmaceutical composition described herein includes an additional active ingredient. In another exemplary embodiment, the additional active ingredient is a compound that has been approved for human use by the United States Food and Drug Administration.

VI. Environmental Bait

In another aspect, the invention provides a composition comprising: a) a compound of the invention; and b) a mouse bah formulation. In an exemplary embodiment, the compound of the invention can be formulated at therapeutic concentrations in standard size mouse food pellets. In an exemplary embodiment, the compound of the invention is water soluble and is directly nixed with the feed prior to forming pellets. In an exemplary embodiment, the pellets can be deployed by scattering in environmental settings with high populations of rodents or placed within T-shaped bait-stations built, of PVC piping that allows feeding by mice but blocks access by humans. Baits can be formulated using Bait Formula supplied by FoodSource or a similar nutrient mouse chow base.

In one example of formulation for a single large bait, 2 g of bait formula is mixed with 0.5 g of peanut butter and 2 mL of boiling water; After mixing and cooling, the compound can be added and stirred together with a sterile spatula. The bait can then be shaped into a square and allowed to air dry at room temperature. Miniature versions can be prepared in wells of a 96-well plate with standard 200 μL working volume. Food coloring may also be added to make the bait more visible to mice (Bhattaeharya et at Vaccine. 2011 Oct. 13; 29(44): 7818-7825).

The invention is further illustrated by the Examples that follow. The Examples are not intended to define or limit the scope of the invention.

EXAMPLES

The following Examples illustrate the synthesis of representative compounds Used in the invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the invention are possible in view of the teachings herein and, therefore, are within the scope of the invention.

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Sigma-Aldrich in Sure-Seal bottles and used as received. All solvents may be purified, using standard methods known to those skilled in the art, unless otherwise indicated. The reactions set forth below were run generally at ambient temperature, unless otherwise indicated. The reaction vessels were fitted with rubber septa for introduction of substrates and reagents via syringe. Analytical thin layer chromatography (TLC) was performed using glass-backed silica gel pre-coated plates (Analtech TLC Uniplates™ with fluorescent indicator) and eluted with appropriate solvent ratios (v/v). Reactions were assayed by TLC or LC/MS, and terminated as judged by the consumption of starting material. Visualization of the TLC plates was done with UV light (254 nm wavelength) or with an appropriate TLC visualizing solvent, such as basic aqueous $KMnO_4$ solution, ninhydrin, cerium molybdate, or phosphomolybdic acid, activated with heat. Flash column chromatography (W. C. Still et al, J. Org. Chem. 43, 1978, 2923-2925) was performed using Biotage Isolera Prime automated flash purification system (220 and 254 nm wavelength) with ZIP Spherespherical Silica or KP Silica cartridges or various preparative HPLC systems. The compound structures in the examples below were confirmed by one or more of the Following methods: proton magnetic resonance spectroscopy, mass spectrometry, and melting point. Proton magnetic resonance (1HNMR) spectra were recorded using an NMR spectrometers operating at 300, 400 or 500 MHz field strength. Chemical shifts are reported in the form of delta (δ) values given in parts per million (ppm) relative to an internal standard, such as tetramethylsilane (TMS). Alternatively, 1HNMR spectra were referenced to signals from residual protons in deuterated solvents as follows: $CDCl_3$=7.25 ppm; DMSO-$d_6$=2.49 ppm; $CD_3OD$=3.30 ppm. Peak multiplicities are designated as follows: s, singlet; d, doublet; dd, doublet of doublets; t, triplet; dt, doublet of triplets, q, quartet; br, broadened; and m, multiplet. Coupling constants are given in Hertz (Hz). Mass spectrometric (MS) data were obtained using a mass spectrometer with APCI or ESI ionization.

Starting materials used were either available from commercial sources or prepared according to literature procedures and had experimental data, in accordance with those reported.

Example 1

Hygromycin A and Analogs

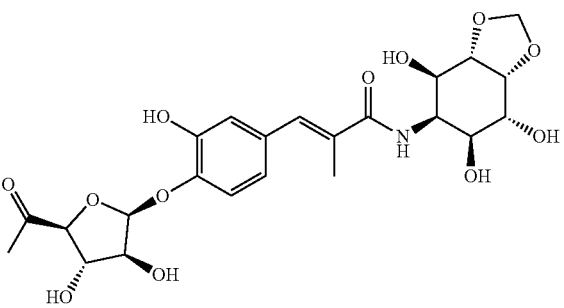 [SMILES: CC(=O)[C@H]1O[C@@H](Oc2ccc(/C=C(\C)C(=O)N[C@@H]3[C@H](O)[C@@H](O)[C@H]4OCO[C@H]4[C@@H]3O)cc2O)[C@@H](O)[C@@H]1O]

Hygromycin A was isolated from culture supernatant of *Streptomyces hygroscopicus*. The strain was incubated in MR5 liquid culture at 28° C. for 10 days with shaking (200 rpm). Culture was centrifuged, and cell pellets were removed. Supernatant was treated with XAD16N resin (20-60 mesh, Sigma-Aldrich). The active fraction containing hygromycin A was eluted from the resin in 100% methanol. Methanol extract was dried using a rotary evaporator, and dried sample was dissolved in MilliQ water. The sample was subjected to preparative high-performance liquid chromatography (HPLC) with $C_{18}$ reverse-phase column (Luna® 5 μm $C_{18}$(2) 100 Å, LC Column 250×21.2 mm) and eluted at a flow rate of 10 ml/min. The HPLC apparatus included a Shimadzu HPLC system equipped with an SPD-M20A diode array detector (SHIMADZU Co. Ltd., Japan). The solvent and conditions used were 0 to 5 min of 7% acetonitrile (ACN) that contained 0.1% formic acid (FA) and 5 to 43 min of a linear gradient of 7 to 15.5% ACN that contained 0.1% FA. Hygromycin A was doted as single peak at retention time 40 min.

Other compounds of the invention can be synthesized according to techniques well known to those skilled in the art.

Example 2

Testing of Hygromycin A Against Certain Bacterial Species: MIC Values

AH MIC testing of bacteria followed the Clinical and Laboratory Standards Institute (CLSI) guidelines for antimicrobial testing of aerobic, bacteria (Methods for Dilution Antimicrobial Susceptibility Tests for Bacteria that Grow Aerobically; Approved Standard—Tenth Edition, M07-A10; Performance Standards for Antimicrobial Susceptibility Testing; Twenty-fifth Informational Supplement, M100-S25), and guidelines for antimicrobial testing of anaerobic bacteria (Methods for Antimicrobial Susceptibility Testing of Anaerobic Bacteria, 8th Edition. M11-A8). Compounds of the invention can also be tested for activity as described herein.

Briefly, the microbroth dilution MIC method was used to quantitatively measure the in vitro antibacterial activity of hygromycin A against the given bacterial isolates shown in the table below. S. aureus, E. coli and P. aeruginosa were grown in cation-adjusted Mueller-Hinton broth, anaerobes were grown in Schaedler Anaerobe Media, Borrelia species were grown in BSK-II medium. Bacteria from liquid cultures were diluted into the assay plate to achieve $5\times10^5$ CFU/mL. Assays plates were prepared by 2-fold dilution of compound across the plate and included a positive growth control. After incubating the aerobes at 37° C. for 16-20 hours and the anaerobes in an anaerobic chamber for 24-48 hours, the MIC was determined as the lowest concentration of compound that inhibits growth of the bacteria as detected by the unaided eye. Borrelia species were incubated in in a microaerophilic chamber at 34° C. for 5-7 days and scored visually for medium color change from pink to yellow of the phenol red present in the medium. The lowest concentration of antibiotics that pre vented color change was interpreted, as the MIC.

| Bacterial Species | MIC (μg/mL) |
| --- | --- |
| Borrelia burgdorferi | 0.12 |
| Borrelia afzelii | 0.25 |
| Borrelia bavariensis | 0.25 |
| Borrelia garinii | 0.25 |
| Borrelia turcica | 0.25 |
| Treponema pallidum | 0.03 |
| Bifidobacterium longum | 8 |
| Lactobacillus reuteri | 32 |
| S. aureus | 32 |
| Bacteroides fragilis | 128 |
| Enterococcus faecalis | 128 |
| E. coli | 1000 |
| P. aeruginosa | >1000 |

Example 3

Testing of Hygromycin A Against C3H Mice Infected with Borrelia burgdorferi

C3H mice (Charles River Laboratories) are used in classical Lyme disease infection model. Mice were rested for more than 1 day after delivery before infected with $10^5$ B. burgdorferi N40 cells by subcutaneous injection. Infection was established for 3 weeks. 100 μl of saline, ceftriaxone or hygromycin A was administered by IP injection. Compounds of the invention can also be tested for efficacy as described herein.

Ceftriaxone (USP grade) was purchased from Sigma-Aldrich. Saline was purchased from Baxter Healthcare. Ceftriaxone powder was dissolved into saline to 31.2 mg/ml solution. Hygromycin A stock solution at 200 mg/ml was diluted into saline to make 50 mg/ml (250 mg/kg), 15 mg/ml (75 mg/kg), 14 mg/ml (70 mg/kg), 10 mg/ml (50 mg/kg) and 5 mg/ml (25 mg/kg) solutions.

In the B. burgdorferi mice infection model, skin is the tissue with highest bacterial burden. After sacrificing mice 2 days after 5 days of dosing, we took 100 mg skin tissue from mouse ear, homogenized the tissue and plated on BSK-II semi-agar plates for cell number counts. No colony appearing on the plates is considered as clearance of the infection.

| Compounds | Dose (mg/kg) | Route | # of B. burgdorferi cells in 100 mg skin tissue |
| --- | --- | --- | --- |
| Saline | | IP injection | 700 |
| Ceftriaxone | 156 | IP injection | <1 |
| Hygromycin A | 75 | IP injection | <1 |
| Hygromycin A | 250 | Oral gavage | <1 |
| Hygromycin A | 70 | Oral gavage | <1 |
| Hygromycin A | 50 | Oral gavage | <1 |
| Hygromycin A | 25 | Oral gavage | <1 |

The table demonstrates that Hygromycin A is active in vivo against Borrelia burgdorferi. Hygromycin A cleared the Borrelia burgdorferi infection in C3H mice after 5 days of treatment administered by both IP injection and oral gavage.

Example 4

Hygromycin A Microbiome Data

In order to examine the effects of hygromycin on the microbiome we determined the relative percent abundance of prominent families in the gut microbiome after treatment with either hygromycin or ampicillin and ceftriaxone controls.

Experimental

Mice were infected with Borrelia burgdorferi N40 via a subcutaneous injection of 10^5 cells per mouse. Following a three-week, incubation period, mice were treated every 12 hours for 5 days with oral hygromycin A (50 mg/kg), IP hygromycin A (50 mg/kg), oral amoxicillin (100 mg/kg), IP amoxicillin (100 mg/kg), or subcutaneous ceftriaxone (156 mg/kg) (n=5/group). In addition, there were uninfected, untreated and infected, untreated controls. Stool was collected in 20% glycerol on dry ice before treatment and after treatment and sequenced by Mr. DNA (Shallowater, TX) as follows. The V4 region of the 16s rRNA gene was amplified using primers 515/806 in a single-step 30 cycle PGR with the HotStarTaq Plus Master Mix Kit (Qiagen, USA). The following conditions were used: 3 minutes at 94° C., 30 cycles of 30 seconds at 94° C., 40 seconds at 53° C., and 1 minute at 72° C., and then 5 minutes at 72° C. Sequencing was performed on an Ion Torrent and analyzed using a proprietary analysis pipeline wherein sequenced were depleted of barcodes and primers, sequences of <150 bp, sequences with homopolymer runs <6 bp, or sequence with ambiguous base calls were removed. The sequences, were then denoised and operational taxonomic units were generated. OTUs were defined by 97% similarity and were taxonomically classified using BLASTn against a database informed by RDPII and NCBI.

Results

The infected, untreated and uninfected, untreated groups had natural shifts in their gut microbiota composition. Ceftriaxone and oral amoxicillin lead to Enterococcaceae blooms, up to 98% relative abundance, in 5/5 and 4/5 mice respectively; all other commensal taxa such as Bacteroidaceae and Lactobacillaceae were depleted in these mice. The average Enterococcaceae increase in oral amoxicillin treated mice was 75.8% relative abundance and 77.7% in ceftriaxone treated mice. In contrast, oral hygromycin treatment did not lead to increases in Enterococcaceae or Enterobacteriaceae. Bacteroidaceae decreased in 3/5 mice treated with oral hygromycin, but 1/5 mice maintained Bacteroidaceae and 1/5 mice had increased Bacteroidaceae, and the overall fluctuation of Bacteroidaceae (−8.5% relative abundance) was not significantly different from the infected, untreated group (−13.3% relative abundance). Oral hygromycin treatment led to an average 31.09% relative abundance increase of Streptococcaceae, represented nearly completely by the genus *Lactococcus*. *Lactococcus* is a genus of food-grade organisms, used in the dairy industry, that is more prominent in the mouse gut microbiome than the human gut microbiome; thus, it is unlikely that this, perturbation would be significant in the human gut microbiome, Overall the disruption to the gut microbiome was considerably less severe than treatment with either ampicillin or ceftriaxone.

Table 1. The average percent relative abundance changes from before treatment to after treatment of all families represented in the C3H mouse gut microbiome. Mice were infected with *Borrelia burgorferi* N40 and treated every 12 hours for 5 days with hygromycin orally or intraperitoneally, amoxicillin orally or IP, or ceftriaxone subcutaneous (n=5 per group). Stool was collected before treatment and after treatment and the 16S rRNA gene was sequenced. The average percent relative abundance of each family was compared from before treatment to after treatment and is reported as the change in percent relative abundance. UI=uninfected, UT=untreated, Hyg=hygromycin A, Amox=amoxicillin, Cef=ceftriaxone, IP=intraperitoneal.

| Family | UI, UT | I, UT | Hyg oral | Hyg IP | Amox oral | Amox IP | Cef |
|---|---|---|---|---|---|---|---|
| Acholeplasmataceae | 0.001 | −0.001 | 0.005 | 0.003 | 0.095 | 0.005 | 0.213 |
| Aerococcaceae | 0.000 | 0.000 | 0.000 | 0.001 | 0.000 | 0.000 | 0.000 |
| Anaerolineaceae | 0.000 | 0.000 | 0.000 | 0.000 | 0.000 | 0.000 | 0.000 |
| Anaeroplasmataceae | 0.005 | −0.026 | −0.016 | −0.007 | −0.048 | −0.132 | 0.000 |
| Anaplasmataceae | 0.000 | 0.000 | 0.000 | 0.000 | 0.000 | 0.000 | 0.001 |
| Aspergillaceae | 0.000 | 0.000 | 0.000 | 0.000 | 0.000 | 0.000 | 0.000 |
| Asteraceae | 0.000 | 0.000 | 0.000 | 0.001 | 0.003 | 0.000 | 0.011 |
| Bacillaceae | −0.001 | −0.011 | −0.009 | −0.021 | 0.002 | −0.011 | 0.055 |
| Bacillales | −0.087 | 0.015 | −0.092 | −0.108 | −0.100 | −0.031 | −0.174 |
| Bacteroidaceae | −2.812 | −13.377 | −8.462 | −14.397 | −8.426 | 0.684 | −26.593 |
| Bifidobacteriaceae | 0.408 | 0.000 | 0.013 | 0.000 | −0.124 | 0.000 | 0.000 |
| Brucellaceae | 0.000 | 0.000 | 0.000 | 0.000 | 0.001 | 0.000 | 0.000 |
| Candidatus saccharibacteria | 0.003 | 0.033 | −0.043 | −0.022 | −0.022 | −0.018 | −0.062 |
| Carnobacteriaceae | 0.001 | −0.001 | 0.005 | −0.001 | −0.002 | 0.000 | 0.000 |
| Chitinophagaceae | 0.000 | 0.000 | 0.000 | 0.000 | 0.000 | 0.000 | 0.000 |
| Christensenellaceae | −0.001 | 0.000 | 0.000 | 0.000 | 0.000 | 0.000 | 0.000 |
| Clostridiaceae | −3.911 | 0.124 | −5.257 | −0.066 | −6.891 | 0.211 | −10.423 |
| Clostridiales | −0.031 | 0.019 | −0.174 | −0.099 | −0.099 | −0.037 | −0.174 |
| Clostridiales family xi. incertae sedis | −0.033 | 0.001 | −0.032 | −0.047 | −0.027 | −0.010 | −0.050 |
| Clostridiales family xiii. incertae sedis | −0.009 | −0.009 | −0.007 | −0.013 | −0.011 | −0.007 | −0.015 |
| Coriobacteriaceae | 0.059 | 0.094 | −0.038 | 0.014 | −0.019 | 0.099 | −0.049 |
| Corynebacteriaceae | 0.000 | 0.001 | 0.000 | 0.000 | 0.000 | 0.000 | 0.002 |
| Cytophagaceae | 0.001 | 0.001 | −0.001 | 0.000 | −0.001 | 0.001 | 0.000 |
| Deferribacteraceae | −0.616 | 0.629 | −1.462 | 0.368 | −0.085 | 0.080 | −1.344 |
| Defluviitaleaceae | −0.001 | −0.005 | −0.002 | −0.001 | −0.001 | 0.000 | −0.002 |
| Desulfobacteraceae | 0.000 | 0.000 | −0.001 | 0.000 | 0.000 | 0.000 | 0.000 |
| Enterobacteriaceae | −0.256 | 0.070 | −0.026 | 1.250 | −1.496 | −0.243 | −0.487 |
| Enterococcaceae | 0.051 | −0.017 | 6.546 | 0.036 | 75.807 | 0.052 | 77.719 |
| Erysipelotrichaceae | 2.390 | −1.151 | 1.506 | 5.307 | −2.932 | −0.193 | −1.012 |
| Eubacteriaceae | −3.779 | −0.905 | −6.405 | 0.037 | 4.510 | −1.475 | −3.445 |
| Fabaceae | 0.000 | 0.000 | 0.000 | 0.000 | 0.001 | 0.000 | 0.003 |
| Flavobacteriaceae | 0.000 | 0.001 | −0.001 | 0.000 | 0.000 | 0.000 | 0.000 |
| Francisellaceae | 0.000 | 0.000 | 0.000 | −0.001 | −0.001 | 0.001 | 0.000 |
| Fusobacteriaceae | 0.000 | 0.000 | 0.000 | 0.000 | 0.000 | 0.000 | 0.001 |

-continued

| Family | UI, UT | I, UT | Hyg oral | Hyg IP | Amox oral | Amox IP | Cef |
|---|---|---|---|---|---|---|---|
| Gammaproteobacteria | −0.005 | −0.006 | −0.025 | −0.020 | −0.027 | 0.003 | −0.008 |
| Gloeobacteraceae | −0.010 | −0.149 | −0.013 | −0.020 | −0.013 | 0.055 | −0.018 |
| Gracilibacteraceae | −0.034 | 0.064 | −0.072 | −0.112 | −0.105 | −0.026 | −0.087 |
| Halomonadaceae | 0.000 | 0.000 | 0.000 | 0.000 | 0.001 | 0.000 | 0.000 |
| Hylidae | 0.000 | 0.000 | 0.000 | 0.000 | 0.002 | 0.000 | 0.001 |
| Kopriimonadaceae | −0.008 | 0.000 | 0.000 | 0.000 | 0.000 | 0.000 | 0.000 |
| Lachnospiraceae | −7.558 | −0.597 | −8.372 | 1.241 | −5.482 | −1.425 | −11.193 |
| Lactobacillaceae | 10.222 | −0.115 | 22.074 | 9.667 | −15.023 | 1.726 | −1.712 |
| Leuconostocaceae | 0.000 | 0.000 | 0.000 | −0.001 | 0.002 | 0.000 | 0.015 |
| Methylobacteriaceae | 0.000 | 0.000 | 0.000 | 0.000 | 0.000 | 0.000 | 0.001 |
| Microbacteriaceae | 0.000 | 0.000 | 0.000 | 0.000 | 0.000 | 0.000 | 0.001 |
| Mucoraceae | 0.000 | 0.000 | 0.000 | 0.000 | 0.002 | 0.000 | 0.000 |
| Nostocaceae | 0.000 | 0.000 | 0.000 | 0.000 | 0.001 | 0.000 | 0.002 |
| Onagraceae | 0.000 | 0.000 | 0.000 | 0.000 | 0.000 | 0.000 | 0.000 |
| Oscillatoriales | 0.000 | −0.001 | 0.001 | 0.000 | 0.069 | 0.000 | 0.090 |
| Oscillospiraceae | −0.004 | 0.000 | −0.009 | −0.009 | −0.005 | 0.001 | −0.009 |
| Paenibacillaceae | −0.002 | 0.001 | −0.002 | −0.001 | −0.001 | −0.001 | 0.003 |
| Pasteurellaceae | 0.000 | 0.000 | 0.000 | 0.000 | 0.000 | 0.000 | 0.001 |
| Pelobacteraceae | 0.000 | 0.000 | 0.000 | 0.000 | 0.000 | 0.000 | 0.000 |
| Peptococcaceae | −0.089 | −0.374 | −0.835 | −0.885 | −0.948 | −0.325 | −0.602 |
| Peptoniphilaceae | 0.000 | 0.000 | 0.000 | 0.000 | 0.000 | 0.000 | 0.001 |
| Peptostreptococcaceae | −0.056 | −0.107 | −0.095 | −0.194 | −0.187 | −0.131 | −0.185 |
| Physalacriaceae | 0.000 | 0.000 | 0.000 | 0.000 | 0.000 | 0.000 | 0.000 |
| Poaceae | 0.002 | −0.008 | 0.007 | 0.019 | 0.107 | 0.024 | 0.820 |
| Polyangiaceae | 0.000 | 0.000 | 0.000 | 0.000 | 0.000 | 0.000 | 0.001 |
| Porphyromonadaceae | 8.148 | 20.982 | −23.435 | −0.221 | −19.192 | 10.471 | −24.493 |
| Prevotellaceae | 0.030 | 0.152 | −0.285 | −0.319 | −0.240 | 0.080 | −0.417 |
| Pseudomonadaceae | 0.000 | 0.000 | 0.000 | 0.000 | 0.000 | 0.000 | 0.002 |
| Rhizobiaceae | 0.000 | 0.000 | 0.000 | 0.000 | 0.001 | 0.000 | 0.001 |
| Rhodobacteraceae | 0.000 | 0.000 | 0.000 | 0.000 | 0.000 | 0.000 | 0.000 |
| Rikenellaceae | −3.873 | −3.190 | −4.391 | −4.710 | −6.166 | −3.443 | −6.750 |
| Ruminococcaceae | −1.168 | −0.480 | −1.494 | 1.486 | −1.440 | −0.093 | −2.217 |
| Sphingomonadaceae | 0.000 | 0.000 | 0.000 | 0.000 | 0.000 | 0.000 | 0.000 |
| Spirochaetaceae | −0.018 | −0.102 | −0.086 | −0.074 | −0.056 | −0.032 | −0.055 |
| Spiroplasmataceae | −0.104 | −0.028 | −0.093 | −0.107 | −0.004 | −0.059 | −0.051 |
| Staphylococcaceae | 0.000 | 0.001 | 0.001 | 0.004 | 0.000 | −0.001 | 0.047 |
| Streptococcaceae | 3.172 | −1.510 | 31.098 | 2.055 | −2.376 | −7.086 | 12.672 |
| Thermoanaerobacteraceae | −0.015 | −0.027 | −0.010 | −0.018 | −0.028 | −0.008 | −0.033 |
| Veillonellaceae | 0.001 | 0.000 | 0.002 | 0.000 | 0.001 | 0.000 | 0.000 |
| Verrucomicrobiaceae | −0.014 | 0.006 | −0.017 | −0.017 | −0.009 | 1.296 | −0.004 |
| Xanthomonadaceae | 0.000 | 0.000 | 0.000 | 0.000 | 0.002 | 0.001 | 0.001 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a disease associated with a spirochete in an animal, comprising: administering to the animal in need of treatment thereof a compound according to formula (XVII), a pharmaceutically acceptable salt, a hydrate, or a solvate thereof:

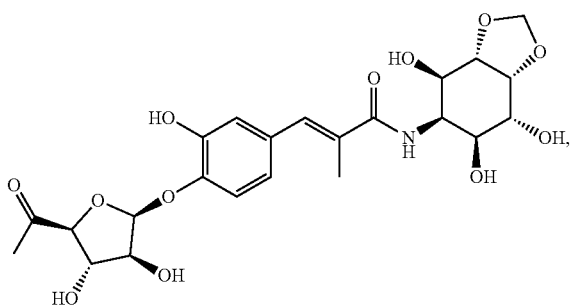

(XVII)

thereby treating the disease associated with the spirochete,
wherein the disease associated with the spirochete is Lyme disease;
wherein treatment with the compound, the pharmaceutically acceptable salt, the hydrate, or the solvate thereof, does not increase relative abundance of Enterococcaceae in the animal; and
wherein the animal is a human.

2. The method of claim 1, wherein the spirochete is *Borrelia burgdorferi*.

3. The method of claim 1, wherein the compound is administered to the animal via an oral route or a parenteral route.

4. The method of claim 3, wherein the compound is administered to the animal via an oral route.

5. The method of claim 3, wherein the compound is administered to the animal via a parenteral route.

6. The method of claim 5, wherein the parenteral route is selected from the group consisting of an intravascular route, a subcutaneous route, an intradermal route, an intramuscular route, a spinal route, and an intrathecal route.

7. The method of claim 1, wherein the compound is administered in an amount from about 5 mg to about 250 mg/kg body weight of the animal.

8. The method of claim 1, wherein the compound is administered in an amount from about 25 mg to about 150 mg/kg body weight of the animal.

9. The method of claim 1, wherein the compound is administered at a dose of 250 mg/kg body weight of the animal.

10. The method of claim 1, wherein the compound is administered at a dose of 70 mg/kg body weight of the animal.

11. The method of claim 1, wherein the compound is administered at a dose of 50 mg/kg body weight of the animal.

12. The method of claim 1, wherein the compound is administered at a dose of 25 mg/kg body weight of the animal.

13. The method of claim 1, wherein the compound is administered at a dose of 75 mg/kg body weight of the animal.

14. A method of killing and/or preventing the growth of a spirochete in an animal, comprising: contacting the spirochete with a compound according to formula (XVII), a pharmaceutically acceptable salt, a hydrate, or a solvate thereof:

(XVII)

thereby killing and/or preventing the growth of the spirochete,
wherein the spirochete is *Borrelia burgdorferi*; and
wherein contact with the compound, the pharmaceutically acceptable salt, the hydrate, or the solvate thereof, does not increase relative abundance of Enterococcaceae in the animal; and
wherein the animal is a human.

15. The method of claim 14, wherein the compound, the pharmaceutically acceptable salt, the hydrate, or the solvate thereof, is administered to the animal via an oral route.

16. The method of claim 14, wherein the spirochete is contacted with the compound at a concentration of 0.12 µg/ml.

17. The method of claim 8, wherein the spirochete is contacted with the compound at a concentration of 0.25 µg/ml.

18. A method of reducing *Borrelia burgdorferi* infection in an animal, the method comprising:
 a. administering to the animal a compound according to formula (XVII), or a pharmaceutically acceptable salt, hydrate, or solvate thereof:

(XVII)

b. obtaining a tissue sample from the animal; and
 c. measuring the number *Borrelia burgdorferi* cells in the tissue from the animal,
 wherein the compound does not increase relative abundance of Enterococcaceae in the animal; and
 wherein the animal is a human.

19. The method of claim 18, wherein the compound is administered in an amount from about 5 mg to about 250 mg/kg body weight of the animal.

20. The method of claim 18, wherein the compound is administered to the animal via an oral route.

* * * * *